(12) United States Patent
Rieger et al.

(10) Patent No.: US 10,888,713 B2
(45) Date of Patent: Jan. 12, 2021

(54) MULTILEAF COLLIMATOR WITH ALTERNATING TRAPEZOIDAL LEAF GEOMETRY DESIGN

(71) Applicants: Varian Medical Systems, Inc., Palo Alto, CA (US); Varian Medical Systems International AG, Steinhausen (CH)

(72) Inventors: Rachel Rieger, Escondido, CA (US); Juha Kauppinen, Espoo (FI); Anthony Magliari, Newark, IL (US); Dusan Baic, Santa Clara, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 17 days.

(21) Appl. No.: 16/236,112

(22) Filed: Dec. 28, 2018

(65) Prior Publication Data

US 2020/0206535 A1    Jul. 2, 2020

(51) Int. Cl.
| | |
|---|---|
| *A61B 6/06* | (2006.01) |
| *A61N 5/10* | (2006.01) |
| *G21K 1/02* | (2006.01) |
| *G21K 1/04* | (2006.01) |
| *G21K 5/04* | (2006.01) |

(52) U.S. Cl.
CPC .............. *A61N 5/1045* (2013.01); *A61B 6/06* (2013.01); *A61N 5/1081* (2013.01); *G21K 1/02* (2013.01); *G21K 1/025* (2013.01); *G21K 1/04* (2013.01); *G21K 1/043* (2013.01); *A61N 2005/1095* (2013.01); *G21K 1/046* (2013.01); *G21K 5/04* (2013.01)

(58) Field of Classification Search
CPC ................... A61B 6/06; A61N 5/1045; A61N 2005/1095; G21K 1/02; G21K 1/025; G21K 1/04; G21K 1/043; G21K 1/046
USPC .............................. 378/64, 65, 147, 150–153
See application file for complete search history.

(56) References Cited

U.S. PATENT DOCUMENTS

| | | | | |
|---|---|---|---|---|
| 4,987,309 | A | * | 1/1991 | Klasen ................. A61N 5/1042 250/492.1 |
| 5,317,616 | A | * | 5/1994 | Swerdloff ................ A61B 6/00 378/65 |
| 5,351,280 | A | * | 9/1994 | Swerdloff ............ A61N 5/1042 378/150 |

(Continued)

OTHER PUBLICATIONS

PCT, International Search Report and Written Opinion of the International Searching Authority in PCT/US2019/066430, dated Mar. 13, 2020, 9 pages.

*Primary Examiner* — Allen C. Ho
(74) *Attorney, Agent, or Firm* — Varian IP Legal

(57) ABSTRACT

A multileaf collimator includes a plurality of beam-blocking leaves of a first type and a plurality of beam-blocking leaves of a second type. The beam-blocking leaves of the first type are alternatingly arranged with the beam-blocking leaves of the second type side by side. Each of the beam-blocking leaves of the first type has a trapezoidal geometry viewed in the leaf longitudinal moving direction comprising a wider end and a narrower end with the wider end being proximal to a source. Each of the beam-blocking leaves of the second type has a trapezoidal geometry viewed in the leaf longitudinal moving direction comprising a wider end and a narrower end with the wider end being distal to the source.

20 Claims, 4 Drawing Sheets

(56) References Cited

U.S. PATENT DOCUMENTS

| | | | | |
|---|---|---|---|---|
| 5,418,827 | A * | 5/1995 | Deasy | A61N 5/103 378/153 |
| 5,625,663 | A * | 4/1997 | Swerdloff | A61N 5/1042 378/113 |
| 5,661,773 | A * | 8/1997 | Swerdloff | A61N 5/1042 378/65 |
| 5,724,400 | A * | 3/1998 | Swerdloff | A61B 6/00 378/150 |
| 6,560,311 | B1 * | 5/2003 | Shepard | A61N 5/1031 378/65 |
| 6,730,924 | B1 * | 5/2004 | Pastyr | A61N 5/1042 250/505.1 |
| 6,984,835 | B2 * | 1/2006 | Harada | A61N 5/1045 250/492.3 |
| 7,507,975 | B2 * | 3/2009 | Mohr | A61N 5/1042 250/492.1 |
| 7,555,103 | B2 * | 6/2009 | Johnsen | G21K 1/04 378/147 |
| 7,742,575 | B2 | 6/2010 | Bourne | |
| 7,856,082 | B2 * | 12/2010 | Flynn | A61N 5/103 250/492.1 |
| 8,637,841 | B2 | 1/2014 | Prince | |
| 8,718,234 | B2 * | 5/2014 | Echner | A61N 5/1045 250/505.1 |
| 9,324,468 | B2 * | 4/2016 | Mansfield | G21K 1/046 |
| 9,443,633 | B2 * | 9/2016 | Orton | G21K 1/046 |
| 9,943,705 | B2 * | 4/2018 | Chappelow | A61N 5/1045 |
| 9,950,193 | B2 * | 4/2018 | Chappelow | A61N 5/1048 |
| 9,966,160 | B2 * | 5/2018 | Kawrykow | G21K 1/046 |
| 9,974,977 | B2 * | 5/2018 | Lachaine | A61B 8/085 |
| 10,026,517 | B2 * | 7/2018 | Constantin | G21K 1/046 |
| 10,128,014 | B2 * | 11/2018 | Xu | G21K 1/046 |
| 10,143,859 | B2 * | 12/2018 | Ollila | A61N 5/1031 |
| 10,166,406 | B2 * | 1/2019 | Nord | A61N 5/1081 |
| 10,272,264 | B2 * | 4/2019 | Ollila | A61N 5/1039 |
| 10,293,184 | B2 * | 5/2019 | Pishdad | A61N 5/1049 |
| 10,307,614 | B2 * | 6/2019 | Schnarr | A61N 5/1031 |
| 10,307,615 | B2 * | 6/2019 | Ollila | A61N 5/1036 |
| 10,434,334 | B2 * | 10/2019 | Wang | A61N 5/1045 |
| 10,449,389 | B2 * | 10/2019 | Ollila | A61N 5/1047 |
| 10,456,597 | B2 * | 10/2019 | Arai | A61N 5/10 |
| 10,485,988 | B2 * | 11/2019 | Kuusela | A61N 5/1031 |
| 10,485,990 | B2 * | 11/2019 | Willcut | G06T 7/30 |
| 10,500,416 | B2 * | 12/2019 | Larkin | A61N 5/1045 |
| 10,500,417 | B2 * | 12/2019 | Kuusela | A61N 5/1045 |
| 10,507,337 | B2 * | 12/2019 | Willcut | A61N 5/1038 |
| 10,512,791 | B2 * | 12/2019 | Kuusela | A61N 5/1045 |
| 10,518,110 | B1 * | 12/2019 | Jimenez-Carvajal | A61N 5/1045 |
| 10,525,283 | B2 * | 1/2020 | MacDonald | A61N 5/1047 |
| 10,537,749 | B2 * | 1/2020 | Isola | A61N 5/1031 |
| 10,573,032 | B2 * | 2/2020 | Xu | A61B 6/4085 |
| 10,583,311 | B2 * | 3/2020 | Bergfjord | A61N 5/1045 |
| 10,695,586 | B2 * | 6/2020 | Harper | A61N 5/1081 |
| 10,751,014 | B2 * | 8/2020 | Naylor | A61N 5/1067 |
| 2012/0043481 | A1 | 2/2012 | Mansfield et al. | |
| 2016/0361566 | A1 | 12/2016 | Larking | |

* cited by examiner

MULTILEAF COLLIMATOR WITH ALTERNATING TRAPEZOIDAL LEAF GEOMETRY DESIGN

TECHNICAL FIELD

This invention relates generally to radiation apparatuses and methods. In particular, various embodiments of multileaf collimators with alternating trapezoidal leaf geometry design are described.

BACKGROUND

Multileaf collimators (MLCs) are widely used in radiotherapy machines to support various forms of treatment including 3D conformal radiation therapy (3D-CRT), intensity-modulated radiotherapy (IMRT), volumetric modulated arc therapy (VMAT), etc. An MLC includes a plurality pairs of beam-blocking leaves arranged in opposing banks. Individual beam-blocking leaves can be independently moved in and out of a radiation beam to block or modify the beam. In use, selected beam-blocking leaves can be positioned in the radiation beam, forming one or more apertures through which the unblocked radiation beam passes. The aperture(s) define(s) the shape of the radiation beam directed to a treatment field at an isocenter.

Tolerance or gap between adjacent beam-blocking leaves in an MLC exists or is provided to allow dynamic linear or longitudinal movement of the leaves. The interleaf gap or tolerance can be a source of radiation leakage in an MLC. The interleaf tolerance may also cause the leaves to flop when the MLC or the gantry supporting the MLC rotates such that the amount of interleaf leakage is unpredictable. Controlling the amount of interleaf leakage for all gantry and collimator angles is also important so that the radiation delivered by the radiation system to the target is of acceptable quality.

To mitigate MLC interleaf leakage, various leaf designs are developed, including "tongue in groove" designs in which steps or similar geometries are provided on the leaf sides so that leaf materials mutually overlap between leaves. Manufacturing of beam-blocking leaves with a "tongue in groove" design can be very expensive. Further, while a "tongue in groove" design may reduce interleaf leakage, it may lead to undesirable underdose effects when MLC treatment fields are combined.

U.S. Pat. No. 7,742,575 B2 discloses an MLC in which the beam-blocking leaves are held to be shifted or orientated such that the sides or faces of the leaves align with a convergence point which offsets the radiation source. As such, beams from the radiation source would strike the beam-blocking leaves at an angle, avoiding the gap between the adjacent leaves through which radiation could pass uninterrupted. The asymmetrical shift of the beam-blocking leaves from the radiation source creates variations in penumbra and resolution across the entire field.

SUMMARY

Embodiments of this disclosure provide for a multileaf collimator (MLC) having an alternating trapezoidal leaf geometry design. The novel leaf geometry design can reduce MLC interleaf leakage, provide predictability of interleaf leakage regardless of dynamic rotation of the MLC, and maintains uniform side leaf penumbra across the treatment field. The flat sided, trapezoidal leaf geometry design allows for reduction of the manufacturing costs of each individual leaf, and thus the MLC.

In one embodiment, a multileaf collimator comprises a plurality of beam-blocking leaves of a first type and a plurality of beam-blocking leaves of a second type. Each of the beam-blocking leaves of the first type has a trapezoidal geometry viewed in the longitudinal moving direction comprising a first lateral side, a second lateral side, a wider end and a narrower end with the wider end being proximal to a source. Each of the beam-blocking leaves of the second type has a trapezoidal geometry viewed in the longitudinal moving direction comprising a first lateral side, a second lateral side, a wider end and a narrower end with the wider end being distal to the source. The beam-blocking leaves of the first type are alternatingly arranged with the beam-blocking leaves of the second type side by side.

The first lateral sides of the trapezoidal geometry of the plurality of beam-blocking leaves of the first type may align to converge to a first point offset from the source. The second lateral sides of the trapezoidal geometry of the plurality of beam-blocking leaves of the first type may align to converge to a second point offset from the source opposite to the first point.

The first lateral sides of the trapezoidal geometry of the plurality of beam-blocking leaves of the second type may align to converge to the second point, and the second lateral sides of the trapezoidal geometry of the plurality of beam-blocking leaves of the second type may align to converge to the first point. The first and second lateral sides of the plurality of beam-blocking leaves of the first type and the first and second lateral sides of the plurality of beam-blocking leaves of the second type may be substantially flat.

In one embodiment, a multi-level multileaf collimator (MLC) comprises a first MLC in a first level distal to a source and a second MLC in a second level proximal to the source. The second MLC comprises a plurality of beam-blocking leaves of a first type and a plurality of beam-blocking leaves of a second type. Each of the beam-blocking leaves of the first type has a trapezoidal geometry viewed in the longitudinal moving direction comprising a first lateral side, a second lateral side, a wider end and a narrower end with the wider end being proximal to a source. Each of the beam-blocking leaves of the second type has a trapezoidal geometry viewed in the longitudinal moving direction comprising a first lateral side, a second lateral side, a wider end and a narrower end with the wider end being distal to the source. The beam-blocking leaves of the first type are alternatingly arranged with the beam-blocking leaves of the second type side by side.

The plurality of beam-blocking leaves of the first MLC may be longitudinally movable in a direction substantially parallel with the longitudinal moving direction of the beam-blocking leaves of the second MLC. Each of the beam-blocking leaves of the first and second types of the second MLC may laterally offset a beam-blocking leaf of the first MLC.

In one embodiment, an apparatus includes a source of radiation, and a multileaf collimator comprising a plurality of beam-blocking leaves of a first type and a plurality of beam-blocking leaves of a second type. Each of the beam-blocking leaves of the first type has a trapezoidal geometry viewed in the longitudinal moving direction comprising a first lateral side, a second lateral side, a wider end and a narrower end with the wider end being proximal to a source. Each of the beam-blocking leaves of the second type has a trapezoidal geometry viewed in the longitudinal moving direction comprising a first lateral side, a second lateral side, a wider end and a narrower end with the wider end being distal to the source. The beam-blocking leaves of the first type are alternatingly arranged with the beam-blocking leaves of the second type side by side.

The source of radiation may be a source of x-rays, a source of gamma rays, a source of protons, or a source of heavy ions.

This Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings provided below, where.

DETAILED DESCRIPTION OF EMBODIMENTS

Referring to FIGS. 1-5, various embodiments of multileaf collimators (MLCs) with an alternating trapezoidal leaf geometry design will now be described.

Figure 1:
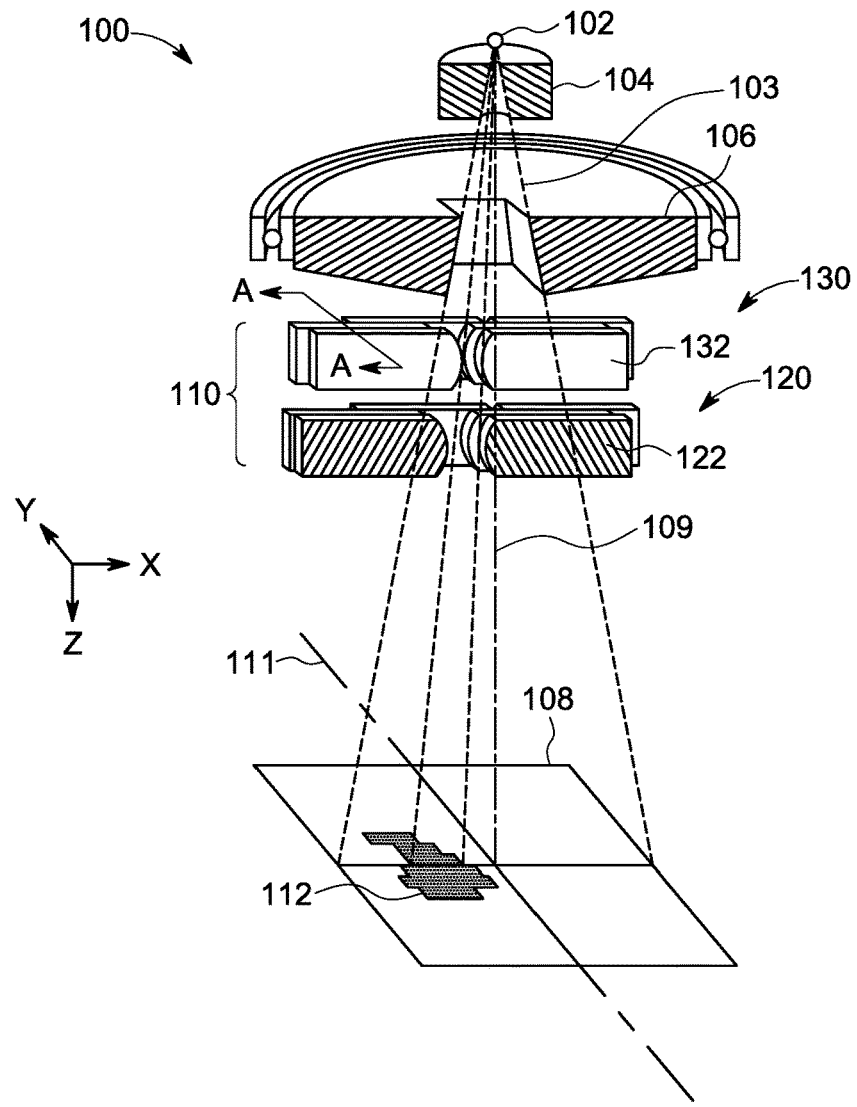
FIG. 1 is a simplified illustration of a radiation system including a multileaf collimator (MLC) in accordance with embodiments of this disclosure.

FIG. 1 is a simplified illustration of a radiation system 100 including an MLC 110 according to embodiments of the disclosure. As shown, the radiation system 100 may include a radiation source 102 configured to produce a beam 103 of radiation such as photons, electrons, protons, or other types of radiation. For example, the radiation source 102 may include a metallic target configured to produce a beam of x-rays upon impingement of electrons. The radiation system 100 may include various beam shaping components such as a primary collimator 104 and optionally a secondary collimator 106 to generally limit the extent of the beam 103 as it travels away from the radiation source 102 toward an isocenter plane 108. An MLC 110 such as a multi-level MLC is disposed between the radiation source 102 and the isocenter plane 108 to further shape the beam 103, as indicated by the shaped field 112 in the isocenter plane 108, according to a general use embodiment of the MLC 110. The MLC 110 may rotate about the beamline or axis 109 passing through the radiation source 102, placing the MLC 110 in various orientations. The radiation source 102, primary collimator 104, secondary collimator 106, and the MLC 110 may be enclosed in a treatment head (not shown), which can be rotated by a gantry (not shown) about an axis such as a horizontal axis 111. Thus, the radiation system 100 can deliver treatment beams to a target in the isocenter plane 108 from various angles. The shape, size, and/or intensity of the beam 103 can be adjusted or dynamically adjusted by the MLC 110 as the beam angle is stepped or swept around the target.

The MLC 110 may be a single level MLC or a multi-level MLC as shown. By way of example, the MLC 110 may include a first MLC 120 in a first level distal to the radiation source 102 and a second MLC 130 in a second level proximal to the radiation source 102. As used herein, the term "multileaf collimator" or "MLC" refers to a collection of a plurality of beam-blocking leaves each of which can be longitudinally moved in and out of a beam 103 to modify one or more parameters of the beam 103 such as the beam shape, size, energy, or intensity etc. Each beam-blocking leaf may be driven by a motor with a lead screw or other suitable means. The beam-blocking leaves may be arranged in pairs. The beam-blocking leaves of each pair may be brought in contact or retracted from each other to close or open a path for a radiation beam to pass through the MLC 110. The beam-blocking leaves may be arranged in opposing banks and supported by a frame, box, carriage or other support structure, which has features allowing the individual beam-blocking leaves to extend into and retract from the beam 103. The frame, box, carriage or other support structure can be further moved or translated in addition to the individual leaf travel.

As shown in FIG. 1, the first MLC 120 and the second MLC 130 may be arranged such that the moving direction of individual beam-blocking leaves of the first MLC 120 and the second MLC 130 are generally in parallel. For example, as shown in FIG. 1 the beam-blocking leaves 122 of the first MLC 120 in the first level are longitudinally movable in the x-direction, and the beam-blocking leaves 132 of the second MLC 130 in the second level are also longitudinally movable in the x-direction. Alternatively, the first MLC 120 and the second MLC 130 may be arranged such that the moving direction of the beam-blocking leaves 122 of the first MLC 120 is non-parallel e.g. perpendicular to the moving direction of the beam-blocking leaves 132 of the second MLC 130.

Figure 2:
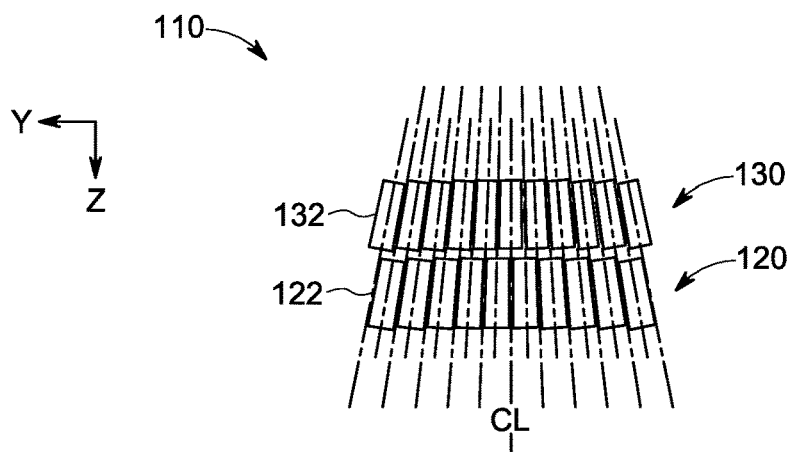
FIG. 2 is a cross-sectional view of the exemplary MLC shown in FIG. 1, taken along line A-A.

The first MLC 120 and the second MLC 130 may be arranged such that the beam-blocking leaves 132 of the second MLC 130 may laterally offset the beam-blocking leaves 122 of the first MLC 120 in a beam's eye view, or as viewed in a direction from the radiation source 102. FIG. 2 is a cross-sectional view of a portion of the multi-level MLC 110 of FIG. 1 taken along line A-A, showing the lateral offset arrangement of the beam-blocking leaves of the multi-level MLC 110. As shown, a beam-blocking leaf 132 of the second MLC 130 in the second level offsets a beam-blocking leaf 122 of the first MLC 120 in the first level as viewed from the radiation source 102. By way of example, a beam-blocking leaf 132 of the second MLC 130 may offset a beam-blocking leaf 122 of the first MLC 120 by substantially half a beam-blocking leaf. Alternatively, a gap between two adjacent beam-blocking leaves 132 of the second MLC 130 in the second level may be positioned substantially at the middle of a beam-blocking leaf 122 of the first MLC 120. The lateral offset arrangement of beam-blocking leaves in different levels provides for leaf projections that are also offset at the isocenter plane 108. Therefore, the lateral offset arrangement of beam-blocking leaves may provide for substantially an equivalent of doubling MLC definition, or improving the resolution to half as compared to the definition of a single level MLC 110 with beam-blocking leaves of the same physical width. In some embodiments, three or more MLCs may be arranged in three or more levels such that each beam-blocking leaf at a level may offset e.g. by ⅓ or 1/n of a leaf width as projected at the isocenter plane 108 where n is the number of the MLCs. U.S. Pat. No. 8,637,841 issued on Jan. 28, 2014 to the common assignee entitled "Multi Level Multileaf Collimators" describes various embodiments of multi-level MLCs, the disclosure of which is incorporated herein by reference in its entirety.

In some embodiments, the MLC 110 may include beam-blocking leaves having a trapezoidal geometry viewed in the beam-blocking leaf longitudinal moving direction. As used herein, the term "trapezoidal geometry" or its grammatic equivalent refers to a geometry including a wider end and a narrower end parallel to each other and two lateral sides connecting the wider end 142 and the narrower end 144. In some embodiments, the lateral sides of the beam-blocking leaves are substantially flat.

Figure 3:
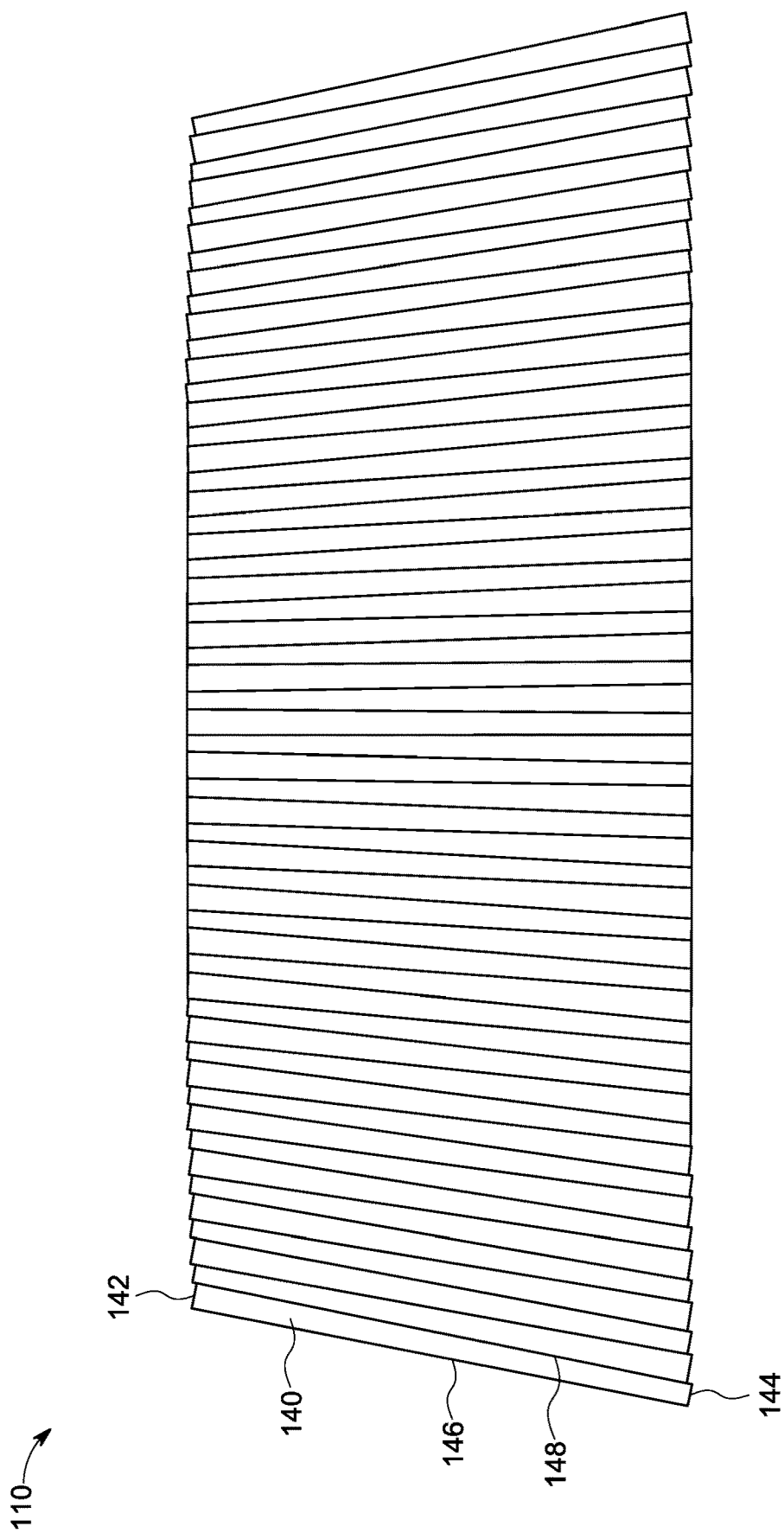
FIG. 3 depicts a bank of beam-blocking leaves of an exemplary MLC as viewed in the leaf longitudinal moving direction according to embodiments of the disclosure.

FIG. 3 depicts a bank of beam-blocking leaves 140 of an exemplary MLC 110 having a trapezoidal geometry design according to embodiments of the disclosure. As shown, a beam-blocking leaf 140 of a trapezoidal geometry design may include a wider end 142 and a narrower end 144 parallel to each other, and a first or left lateral side 146 and a second or right lateral side 148 connecting the wider end 142 and the narrower end 144.

In some specific embodiments, the plurality of beam-blocking leaves 140 of trapezoidal geometry design may be arranged such that the beam-blocking leaves 140 whose wider ends 142 are proximal to the radiation source 102 alternate with the beam-blocking leaves 140 whose wider ends 142 are distal to the radiation source 102. For ease of description, in the Detailed Description and Claims, the term "beam-blocking leaf of a first type" or its grammatic equivalent may be used to refer to a beam-blocking leaf 140 having a trapezoidal geometry with the wider end 142 being arranged proximal to the radiation source 102. The term "beam-blocking leaf of a second type" or its grammatic equivalent may be used to refer to a beam-blocking leaf 140 having a trapezoidal geometry with the wider end 142 being arranged distal to the radiation source 102. Therefore, according to embodiments of the disclosure, the MLC 110 may include a plurality of beam-blocking leaves 140 of a first type and a plurality of beam-blocking leaves 140 of a second type, where the beam-blocking leaves 140 of the first type are alternatingly arranged with the beam-blocking leaves 140 of the second type side by side.

Figure 4:
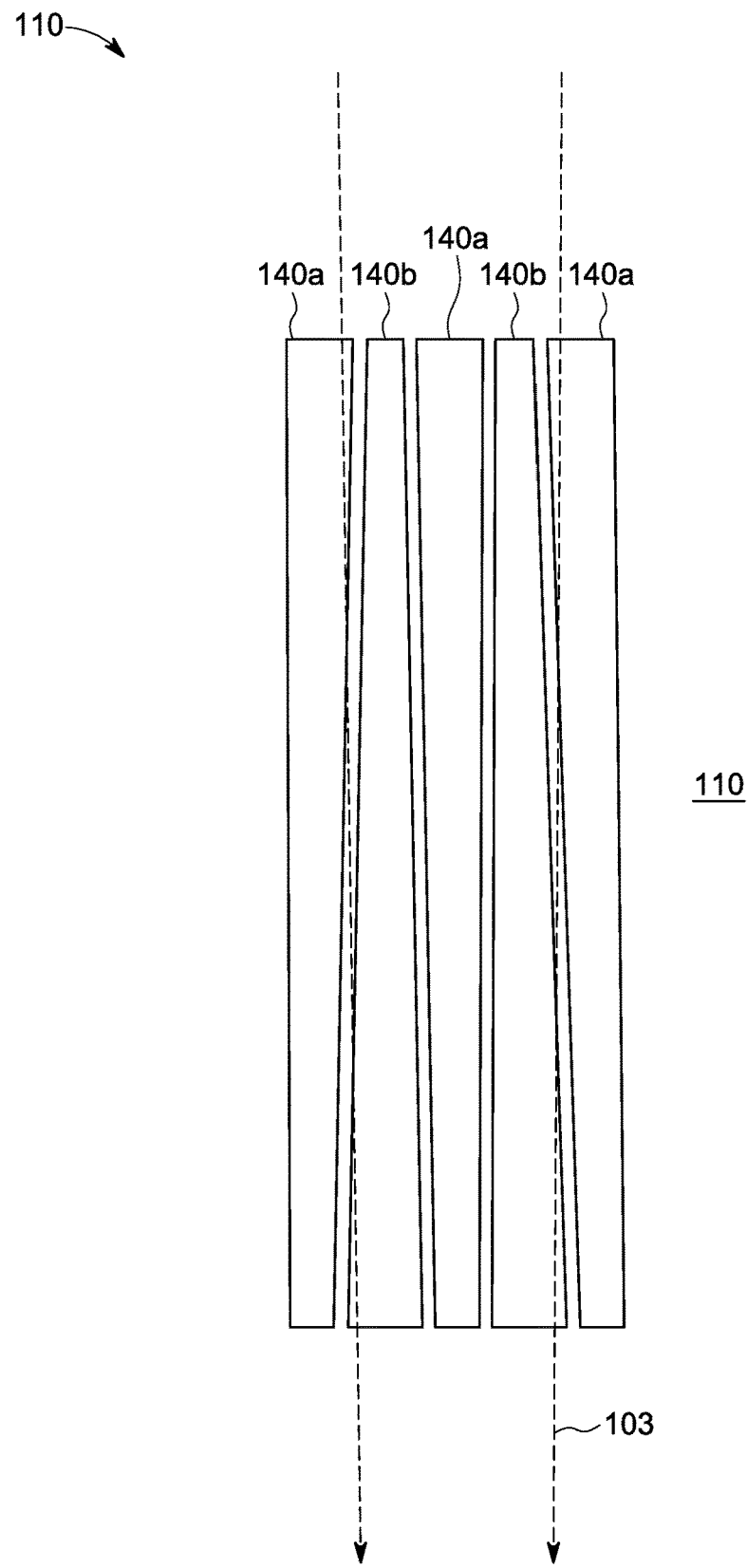
FIG. 4 depicts a sub-set of beam-blocking leaves in the exemplary MLC shown in FIG. 3 according to embodiments of the disclosure.

FIG. 4 illustrates a sub-set of beam-blocking leaves 140 in an exemplary MLC 110 according to embodiments of the disclosure, showing the alternating arrangement of the beam-blocking leaves 140. As shown, each of the beam-blocking leaves 140 has a trapezoidal geometry design as viewed in the leaf longitudinal moving direction. The MLC 110 includes beam-blocking leaves of the first type 140*a*, with the wider end 142 being proximal to the radiation source 102, and beam-blocking leaves of the second type 140*b*, with the wider end 142 being distal to the radiation source 102. The beam-blocking leaves of the first type 140*a* alternate with the beam-blocking leaves of the second type 140*b* side by side.

According to embodiments of the disclosure, the beam-blocking leaves of the first type 140*a* and the beam-blocking leaves of the second type 140*b* can be designed and constructed such that when fitted, the first or left lateral sides 146 of the beam-blocking leaves of the first type 140*a* align to converge to a first point offset from the radiation source 102, and the second or right lateral sides 148 of the beam-blocking leaves of the first type 140*a* align to converge to a second point offset from the radiation source 102. For the beam-blocking leaves of the second type 140*b*, the first or left lateral sides 146 of the beam-blocking leaves 140*b* may align to converge to the second point offset from the radiation source 102 and the second or right lateral sides 148 align to converge to the first point offset from the radiation source 102.

Figure 5:
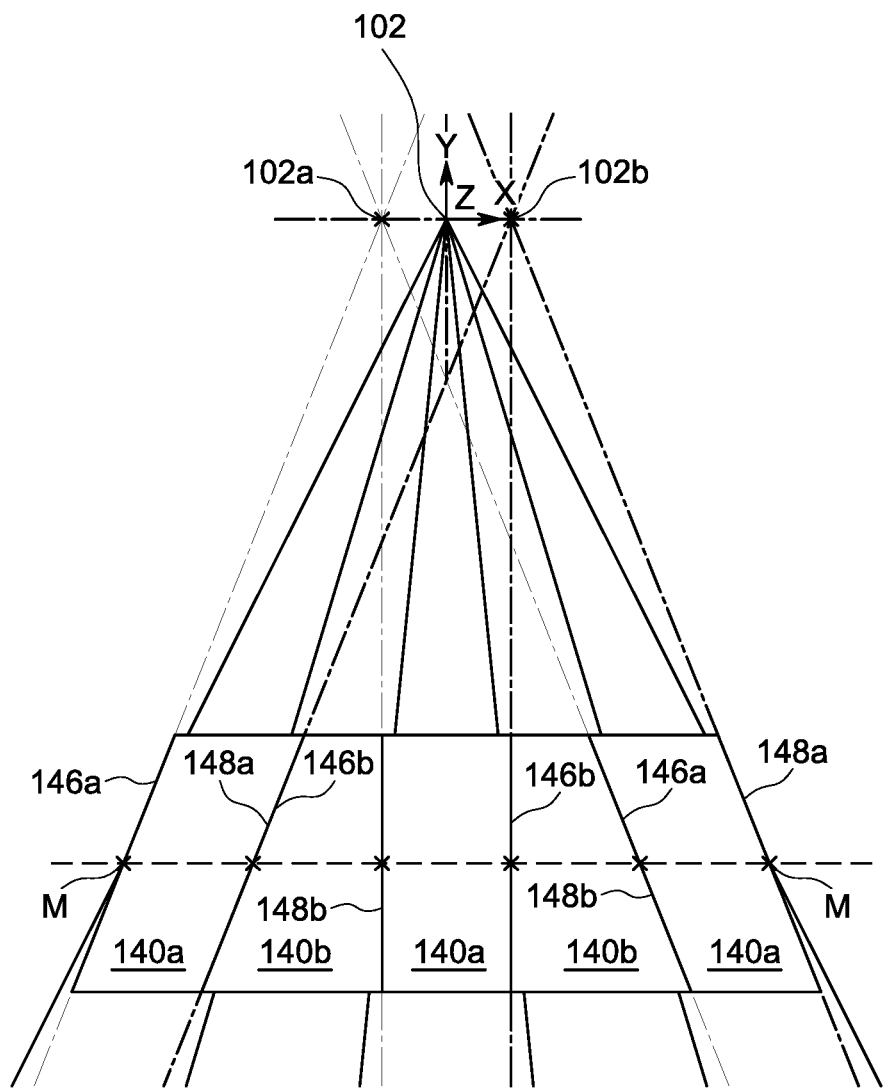
FIG. 5 illustrates various features of an alternating trapezoidal leaf geometry design of an MLC according to embodiments of the disclosure.

Referring to FIG. 5, for example, the left or first lateral sides 146*a* of the plurality of beam-blocking leaves of the first type 140*a* align to converge to a point 102*a*, which offsets the radiation source 102 at a distance (−X). The right or second lateral sides 148*a* of the plurality of beam-blocking leaves of the first type 140*a* align to converge to a point 102*b* which offsets the radiation source 102 at a distance (+X).

Still referring to FIG. 5, the left or first lateral sides 146*b* of the plurality of beam-blocking leaves of the second type 140*b*, which face or are adjacent to the right or second lateral sides 148*a* of the beam-blocking leaves of the first type 140*a*, align to converge to the second point 102*b*, which offsets the radiation source 102 at a distance (+X). The right or second lateral sides 148*b* of the plurality of beam-blocking leaves of the second type 140*b*, which face or are adjacent to the left or first sides 146*a* of the beam-blocking leaves of the first type 140*a*, align to converge to the first point 102*a*, which offsets the radiation source 102 at a distance (−X). The first converging point 102*a* may offset the radiation source 102 at a distance substantially equal to the distance that the second converging point 102*b* offsets the radiation source 102 at an opposite side.

The alternating trapezoidal geometry design of the beam-blocking leaves allows the flat side surfaces of adjacent leaves to be slightly "off-focus" relative to the radiation source 102, hence change the angle of the path or gap between adjacent beam-blocking leaves that a radiating beam from the radiation source 102 would pass. As shown in FIG. 5, the left lateral side 146*a* of beam-blocking leaf 140*a* forms an angle with a line passing the middle point (M) of the lateral side 146*a* and the radiation source 102. Similarly, the right lateral side 148*a* of beam-blocking leaf 140*a* forms an angle with a line passing the middle point (M) of the right lateral side 148*a* and the radiation source 102. These angles allow a radiation beam from the radiation source 102 to be attenuated by both a top corner of a beam-blocking leaf and a bottom corner of an adjacent beam-blocking leaf, thereby reducing interleaf leakage. The plurality of beam-blocking leaves 140 can be designed and constructed such that these off-focus angles are consistent for each of the beam-blocking leaves regardless of the location of the leaf in the leaf bank, providing symmetrical penumbra and resolution for the entire treatment field.

The alternating trapezoidal leaf geometry design provides for improved packing of drive motors for the beam-blocking leaves because it can slit half of the motors to the proximal part of the leaf bank and half of the motors to the distal part of the leaf bank. This provides for more room for the leaf drive system including motors, lead screws etc., allowing for a more robust and reliable design.

The alternating trapezoidal leaf geometry design can also reduce the costs of constructing an MLC because the boxes or support structures for both banks of the beam-blocking leaves can be made identical, reducing the number of parts and ultimately reducing the costs.

Various embodiments of multileaf collimators have been described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. Further, the term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise.

Various relative terms such as "upper," "above," "top," "over," "on," "below," "under," "bottom," "higher," "lower," "left," "right" or similar terms may be used herein for convenience in describing relative positions, directions, or spatial relationships in conjunction with the drawings. The use of the relative terms should not be construed as to imply a necessary positioning, orientation, or direction of the structures or portions thereof in manufacturing or use, and to limit the scope of the invention.

Those skilled in the art will appreciate that various other modifications may be made. All these or other variations and modifications are contemplated by the inventors and within the scope of the invention.

What is claimed is:

1. A multileaf collimator, comprising:
a plurality of beam-blocking leaves of a first type, each of the plurality of beam-blocking leaves of the first type having a trapezoidal geometry viewed in a longitudinal moving direction with a first lateral side, a second lateral side, a wider end, and a narrower end, the wider end being proximal to a source;
a plurality of beam-blocking leaves of a second type, each of the plurality of beam-blocking leaves of the second type having a trapezoidal geometry viewed in the longitudinal moving direction with a first lateral side, a second lateral side, a wider end, and a narrower end, the wider end being distal to the source; and
the plurality of beam-blocking leaves of the first type being alternatingly arranged with the plurality of beam-blocking leaves of the second type side by side.

2. The multileaf collimator of claim 1, wherein
first lateral sides of the plurality of beam-blocking leaves of the first type align to converge to a first point offset from the source, and
second lateral sides of the plurality of beam-blocking leaves of the first type align to converge to a second point offset from the source and opposite to the first point.

3. The multileaf collimator of claim 2, wherein
wherein a first lateral side of a beam-blocking leaf of the second type is adjacent to a second lateral side of a beam-blocking leaf of the first type, and a second lateral side of a beam-blocking leaf of the second type is adjacent to a first lateral side of a beam-blocking leaf of the first type, and
first lateral sides of the plurality of beam-blocking leaves of the second type align to converge to the second point, and second lateral sides of the plurality of beam-blocking leaves of the second type align to converge to the first point.

4. The multileaf collimator of claim 3, wherein the first point offsets from the source at a distance substantially equal to a distance that the second point offsets from the source.

5. The multileaf collimator of claim 1, wherein a first lateral side and a second lateral side of each of the plurality of beam-blocking leaves of the first type, and a first lateral side and a second lateral side of each of the plurality of beam-blocking leaves of the second type are substantially flat.

6. The multileaf collimator of claim 5, wherein the first point offsets from the source at a distance substantially equal to a distance that the second point offsets from the source.

7. The multileaf collimator of claim 1, wherein a first lateral side and a second lateral side of each of the plurality of beam-blocking leaves of the first type, and a first lateral side and a second lateral side of each of the plurality of beam-blocking leaves of the second type are substantially flat.

8. A multi-level multileaf collimator (MLC), comprising:
a first MLC in a first level distal to a source; and
a second MLC in a second level proximal to the source, wherein the second MLC comprises:
a plurality of beam-blocking leaves of a first type, each of the plurality of beam-blocking leaves of the first type having a trapezoidal geometry viewed in a longitudinal moving direction with a first lateral side, a second lateral side, a wider end and a narrower end, the wider end being proximal to the source;
a plurality of beam-blocking leaves of a second type, each of the plurality of beam-blocking leaves of the second type having a trapezoidal geometry viewed in the longitudinal moving direction with a first lateral side, a second lateral side, a wider end, and a narrower end, the wider end being distal to the source; and
the plurality of beam-blocking leaves of the first type being alternatingly arranged with the plurality of beam-blocking leaves of the second type side by side.

9. The multi-level multileaf collimator of claim 8, wherein
first lateral sides of the plurality of beam-blocking leaves of the first type align to converge to a first point offset from the source, and
second lateral sides of the plurality of beam-blocking leaves of the first type align to converge to a second point offset from the source opposite to the first point.

10. The multi-level multileaf collimator of claim 9, wherein
wherein a first lateral side of a beam-blocking leaf of the second type is adjacent to a second lateral side of a beam-blocking leaf of the first type, and a second lateral side of a beam-blocking leaf of the second type is adjacent to a first lateral side of a beam-blocking leaf of the first type, and first lateral sides of the plurality of beam-blocking leaves of the second type align to converge to the second point, and second lateral sides of the plurality of beam-blocking leaves of the second type align to converge to the first point.

11. The multi-level multileaf collimator of claim 10, wherein the first point offsets from the source at a distance substantially equal to a distance that the second point offsets from the source.

12. The multi-level multileaf collimator of claim 8, wherein a first lateral side and a second lateral side of each of the plurality of beam-blocking leaves of the first type, and a first lateral side and a second lateral side of each of the plurality of beam-blocking leaves of the second type are substantially flat.

13. The multi-level multileaf collimator of claim 8, wherein the first MLC comprises a plurality of beam-blocking leaves, each being longitudinally movable in a direction substantially parallel with the longitudinal moving direction of the plurality of beam-blocking leaves of the first type and the plurality of beam-blocking leaves of the second type of the second MLC.

14. The multi-level multileaf collimator of claim 13, wherein each of the plurality of beam-blocking leaves of the first type and the plurality of beam-blocking leaves of the second type of the second MLC laterally offsets a beam-blocking leaf of the first MLC.

15. An apparatus, comprising:
a source of radiation, and
a multileaf collimator comprising:
   a plurality of beam-blocking leaves of a first type, each of the plurality of beam-blocking leaves of the first type having a trapezoidal geometry viewed in a longitudinal moving direction with a first lateral side, a second lateral side, a wider end, and a narrower end, the wider end being proximal the source of radiation;
   a plurality of beam-blocking leaves of a second type, each of the plurality of beam-blocking leaves of the second type having a trapezoidal geometry viewed in the longitudinal moving direction with a first lateral side, a second lateral side, a wider end, and a narrower end, the wider end being distal to the source of radiation; and
   the plurality of beam-blocking leaves of the first type being alternatingly arranged with the plurality of beam-blocking leaves of the second type side by side.

16. The apparatus of claim 15, wherein the source of radiation comprises a source of x-rays, a source of gamma rays, a source of protons, or a source of heavy ions.

17. The apparatus of claim 15, wherein the multileaf collimator comprises a first multileaf collimator in a first level distal to the source of radiation and a second multileaf collimator in a second level proximal to the source of radiation, wherein the plurality of beam-blocking leaves of the first type and the plurality of beam-blocking leaves of the second type are arranged in the second multileaf collimator.

18. The apparatus of claim 17, wherein the first multileaf collimator comprises a plurality of beam-blocking leaves, and each of the plurality of beam-blocking leaves of the first type and the plurality of beam-blocking leaves of the second type of the second multileaf collimator laterally offsets one of the plurality of beam-blocking leaves of the first multileaf collimator.

19. The apparatus of claim 15, wherein
first lateral sides of the plurality of beam-blocking leaves of the first type align to converge to a first point offset from the source, and
second lateral sides of the plurality of beam-blocking leaves of the first type align to converge to a second point offset from the source opposite to the first point.

20. The apparatus of claim 19, wherein
a first lateral side of a beam-blocking leaf of the second type is adjacent to a second lateral side of a beam-blocking leaf of the first type, and a second lateral side of a beam-blocking leaf of the second type is adjacent to a first lateral side of a beam-blocking leaf of the first type, and
first lateral sides of the plurality of beam-blocking leaves of the second type align to converge to the second point, and second lateral sides of the plurality of beam-blocking leaves of the second type align to converge to the first point.

* * * * *